(12) United States Patent
Winter et al.

(10) Patent No.: US 8,008,536 B2
(45) Date of Patent: *Aug. 30, 2011

(54) SIMULATED MOVING BED ADSORPTIVE SEPARATION PROCESS FOR HANDLING MULTIPLE FEEDSTOCKS

(76) Inventors: George R. Winter, Fond Du Lac, WI (US); John M. Stec, Northfield, IL (US)

( * ) Notice: Subject to any disclaimer, the term of this patent is extended or adjusted under 35 U.S.C. 154(b) by 307 days.

This patent is subject to a terminal disclaimer.

(21) Appl. No.: 12/217,696

(22) Filed: Jul. 8, 2008

(65) Prior Publication Data

US 2009/0105515 A1 Apr. 23, 2009

Related U.S. Application Data

(63) Continuation-in-part of application No. 11/047,984, filed on Feb. 2, 2005, now Pat. No. 7,396,973.

(51) Int. Cl.
*C07C 7/12* (2006.01)
(52) U.S. Cl. ........ 585/820; 585/822; 585/823; 585/824; 585/825; 585/829; 585/828
(58) Field of Classification Search .................. None
See application file for complete search history.

(56) References Cited

U.S. PATENT DOCUMENTS

| | | |
|---|---|---|
| 2,985,589 A | 5/1961 | Broughton et al. |
| 3,040,777 A | 6/1962 | Carson et al. |
| 3,201,491 A | 8/1965 | Stine et al. |
| 3,422,848 A | 1/1969 | Liebman et al. |
| 3,686,342 A | 8/1972 | Neuzil |
| 3,706,812 A | 12/1972 | Derosset et al. |
| 3,715,409 A | 2/1973 | Broughton |
| 4,031,156 A | 6/1977 | Geissler et al. |
| 4,313,015 A | 1/1982 | Broughton |
| 4,402,832 A | 9/1983 | Gerhold |
| 4,478,721 A | 10/1984 | Gerhold |
| 4,642,397 A | 2/1987 | Zinnen et al. |
| 4,791,235 A | 12/1988 | Maki et al. |
| 4,793,984 A | 12/1988 | Lok et al. |

(Continued)

FOREIGN PATENT DOCUMENTS

WO WO 95/07740 3/1995

OTHER PUBLICATIONS

Chemical Engineering Progress, vol. 66, No. 9, Sep. 1970, The Parex Process For Recovering Paraxylene, pp. 70-75.

(Continued)

*Primary Examiner* — Tam M Nguyen
(74) *Attorney, Agent, or Firm* — Ryan Kromholz & Manion, S.C.

(57) ABSTRACT

An improved process for the production capacity and feedstock handling flexibility of a simulated moving bed adsorptive separation process by introducing a second feed stream to the adsorbent chamber comprising a feed material of a different concentration of the desired compound than the concentration of the desired compound in the first feed material stream. The introduction of this second feed material stream may be performed at any location on the adsorbent chamber between (i) a transfer point located immediately upstream of the point of the raffinate material stream withdrawal from the adsorbent chamber to (ii) a transfer point located immediately downstream of the point of extract material stream withdrawal from the adsorbent chamber. A recycle stream may be introduced into the system at a location having a concentration similar to the concentration of the first feed material stream.

20 Claims, 4 Drawing Sheets

U.S. PATENT DOCUMENTS

| | | |
|---|---|---|
| 4,835,334 A | 5/1989 | Hobbs et al. |
| 5,912,395 A | 6/1999 | Noe |
| 6,284,695 B1 | 9/2001 | Winter |
| 6,303,021 B2 | 10/2001 | Winter et al. |
| 6,342,649 B1 | 1/2002 | Winter et al. |
| 6,380,438 B1 | 4/2002 | Winter |
| 6,706,938 B2 | 3/2004 | Roeseler et al. |
| 2001/0001451 A1 | 5/2001 | Winter et al. |
| 2002/0071796 A1 | 6/2002 | Winter et al. |

OTHER PUBLICATIONS

Adsorptive Separations by Simulated Moving Bed Technology: The Sorbex Process, D.B. Broughton and S.A. Gembicki, pp. 115-124, (1980).

SIMULATED MOVING BED ADSORPTIVE SEPARATION PROCESS FOR HANDLING MULTIPLE FEEDSTOCKS

RELATED APPLICATIONS

The present application is a continuation-in-part of application Ser. No. 11/047,984, filed on 2 Feb. 2005, now U.S. Pat. No. 7,396,973, issued 8 Jul. 2008.

BACKGROUND OF THE INVENTION

1. Field of the Invention

The subject invention relates to a process for the adsorptive separation of hydrocarbons. More specifically, the invention relates to a process for the continuous simulated countercurrent and co-current adsorptive separation of hydrocarbons.

The polyester fabrics and articles which are in wide use today are produced from a polymer of ethylene glycol and terephthalic acid. Terephthalic acid is produced by the oxidation of high-purity para-xylene. Para-xylene is typically recovered from a predominantly $C_8$ aromatic hydrocarbon fraction derived from various sources such as catalytic reforming by liquid-liquid extraction and/or fractional distillation. The para-xylene is commercially separated from a para-xylene containing feed stream, usually containing all four $C_8$ aromatic isomers, by either crystallization or adsorptive separation or a combination of these two techniques. Adsorptive separation is the newer technique and has captured the great majority of the market share of newly constructed plants for the production of para-xylene.

Essentially all of the commercial adsorptive separation units use a simulated countercurrent movement of the adsorbent and the xylene containing feed stream. This simulation is performed using established commercial technology wherein the adsorbent is held in place in one or more cylindrical adsorbent chambers and the positions at which the streams involved in the process enter and leave the chambers are periodically shifted along the length of the beds. Normally there are at least four streams (feed, desorbent, extract, and raffinate) employed in this procedure. The location at which the feed and desorbent streams enter the chamber and the extract and raffinate streams leave the chamber are simultaneously shifted in the same direction at set intervals. Each shift in location of these transfer points delivers or removes liquid from a different bed within the chamber. This shifting could be performed using a dedicated transfer line for each stream at the entrance to each bed. However, this will greatly increase the cost of the process, and therefore the transfer lines are reused and each transfer line carries each one of the streams at some point in a cycle.

New and efficient chemical process technologies (e.g., XyMax®, Isomar®, pxMax®, XyMaxAE® and Tatoray® for the production of mixed aromatics, and Sarex™ a process marketed by UOP LLC for the production of mixed sugars) have presented the modern refiner with a dilemma of sorts, that is, how to accommodate the ever-changing availability of feedstocks of varying compositions in a process plant of relatively fixed architecture, without the need to perform major process piping and/or equipment revamp work.

2. Description of the Related Art

The general technique employed in the performance of a simulated moving bed adsorptive separation is well described in the open literature. For instance, a general description directed to the recovery of para-xylene was presented at page 70 of the September 1970 edition of Chemical Engineering Progress (Vol. 66, No. 9). A generalized description of the process with an emphasis on mathematical modeling was given at the International Conference on "Fundamentals Of Adsorption", Schloss Elmau, Upper Bavaria, Germany, on May 6-11, 1983, by D. B. Broughton and S. A. Gembicki. U.S. Pat. No. 4,029,717 issued to F. J. Healy et al. describes a simulated countercurrent moving bed adsorptive separation process for the recovery of para-xylene from a mixture of xylene isomers. Numerous other available references describe many of the mechanical parts of a simulated moving bed system, including rotary valves for distributing various liquid flows, the internals of the adsorbent chambers, and control systems.

U.S. Pat. No. 3,686,342 issued to R. W. Neuzil describes the separation of para-xylene from mixed xylenes using simulated countercurrent adsorption employing a zeolitic adsorbent and para diethylbenzene as the desorbent. This combination is a good representation of a commercial operation for this particular separation.

For purposes of explaining the transfer line apparatus employed by the present invention, reference is made to U.S. Pat. No. 3,201,491 issued to L. O, Stine and D. B. Broughton and International Application WO 95/07740. That art includes recognition that the presence of residual compounds in the transfer lines can have some detrimental effects on a simulated countercurrent moving bed process, and which art addresses the flushing of the line used to deliver the feed stream to the adsorbent chamber as a means to increase the purity of the recovered extract or sorbate component. The foregoing patents teach the use of (a) only one feed stream and (b) a line flush only through the one transfer line most immediately previously used to convey feed to the adsorbent chambers, to avoid contamination of the extract stream with the raffinate components of the feed remaining in this transfer line when it is subsequently used to withdraw the extract stream from the chamber as the transfer lines are shifted, as aforesaid. The foregoing references employ a desorbent rich stream to flush the contents of this transfer line back into the adsorbent chamber.

U.S. Pat. No. 3,732,325 issued to Broughton is directed to an improvement to a simulated countercurrent moving bed adsorptive separation process characterized as related to the recycle of extract material from the extract product stream to the purification zone. This patent teaches the use of only one feed stream. Broughton further teaches the introduction of that single feed material stream to the bottom (i.e., the point closest to the point of introduction and upstream of the feed material) of the purification zone.

U.S. Pat. No. 4,031,156 issued to P. R. Geissler et al. is directed to an improvement to a simulated countercurrent moving bed adsorptive separation process characterized as related to flush streams used in the process. This reference is directed to flushing the interstitial void spaces between adsorbent particles in the adsorbent chamber. This patent teaches the use of dual desorbent streams and also teaches the use of only a single feed stream.

U.S. Pat. No. 5,912,395 issued to Noe, directed to an improvement to a simulated countercurrent moving bed adsorptive separation process, is characterized as related to flush streams used in the process. This reference is directed to the flushing of the transfer line most recently used to withdraw a raffinate material stream from the adsorbent chamber only with a single feed material stream. This reference does not teach means to accommodate more than one feed stream material.

Relative selectivity, ($\beta$), as used throughout this specification is defined as the ratio of the two components in the adsorbed phase divided by the ratio of the same two components in the unabsorbed phase at equilibrium conditions. The equilibrium conditions are determined when the feed passing over a bed of adsorbent does not change composition, in other words, when there is no net transfer of material occurring between the unabsorbed and adsorbed phases. Relative selectivity can be expressed not only for one feed compound as compared to another but can also be expressed between any feed mixture component and the desorbent material.

Where relative selectivity of two components approaches 1.0, there is no preferential adsorption of one component by the adsorbent with respect to the other; they are both adsorbed to about the same degree with respect to each other. As P becomes less than or greater than 1.0, there is a preferential adsorption by the adsorbent for one component with respect to the other. When comparing the selectivity of the adsorbent for component C over component D, a β larger than 1.0 indicates preferential adsorption of component C within the adsorbent. A β less than 1.0 indicates that component D is preferentially adsorbed leaving an unabsorbed phase richer in component C and an adsorbed phase richer in component D.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and, therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material, and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

SUMMARY OF THE INVENTION

The present invention discloses a means to improve the production capacity and feedstock handling flexibility of a simulated countercurrent moving bed adsorptive separation process by introducing a second distinct feed stream to the adsorbent chamber, such second feed stream comprising a feed material of a different concentration of the desired compound than the concentration of such desired compound contained in the first feed material stream. Alternatively, the invention can be practiced by having a second feed in which the ratio of the concentration of the desired compounds to one of the undesirable compounds is different from the first feed.

The present invention is an improvement to simulated countercurrent moving bed adsorptive separation processes and includes the step of introducing into the process a second feed material stream of distinct composition from the first feed material stream, whereby the capacity and feedstock handling flexibility of the process is increased.

The introduction of the second feed material stream may be at any location on the adsorbent chamber between (i) a transfer point located immediately upstream of the point of the raffinate material stream withdrawal transfer point from the adsorbent chamber to (ii) a transfer point located immediately downstream of the point of extract material stream withdrawal transfer point from the adsorbent chamber. The specific transfer point used for the introduction of the second feed material stream will depend upon the concentration of the desired component and the concentration of the undesired components in the second feed material stream.

According to one aspect of the present invention, the location of introduction of the second feed material stream to the process is selected from an available transfer point on the adsorbent chamber where the adsorbed component composition of the interstitial void space liquid is determined by analysis or calculation to most closely match that of the adsorbed component composition of the second feed material stream. For example, in the case of an extract component rich second feed material the second feed material stream is typically introduced to the process via the transfer line just previously used to supply the first feed material stream to the adsorbent chamber. Alternately, depending on the concentration of the desired component in the second feed material stream, the second feed material may be introduced through any existing transfer point located between the points immediately: (a) downstream of the point of extract material stream withdrawal transfer point from the adsorbent chamber and (b) upstream of the point of raffinate material stream withdrawal transfer point from the adsorbent chamber.

The present invention results in an increased capacity of the process unit and provides for more flexibility in the number and types of feed materials that may be processed therein, all without the need to perform major process piping and/or equipment revamp work.

A preferred application of the process is the separation of olefinic hydrocarbons and non-olefins from a feed mixture comprising olefins and non-olefins using a particular adsorbent and a particular desorbent. A further preferred application of the process is the separation of paraffinic hydrocarbons, such as branched chain paraffin hydrocarbons and straight chain paraffin hydrocarbons from a feed mixture comprising branched chain paraffin hydrocarbons and straight chain paraffin hydrocarbons using a particular adsorbent and a particular desorbent. A yet further preferred application of the process is the separation of sugars such as fructose and glucose from a feed mixture comprising fructose and glucose using a particular adsorbent and a particular desorbent. A most preferred application of the process is the separation of aromatic hydrocarbons such as the separation of para-xylene from a feed mixture comprising at least one other isomer of para xylene, and the para-isomer, using a zeolitic adsorbent and a particular desorbent.

It is an objective of the subject invention to provide an improved process for the simulated moving bed adsorptive separation of chemical compounds. It is a further objective to provide an improved process for the adsorptive separation of aromatic hydrocarbons. It is another objective of the subject invention to provide a process which increases the capacity of a simulated moving bed adsorptive separation process to recover a selectively adsorbed compound. It is a specific objective to increase the capacity of a simulated moving bed process unit to recover para-xylene from a feed stream comprising a mixture of isomers of $C_8$ aromatics. It is yet another specific objective of the present invention to provide for more flexibility in the number and types of feed materials that may be processed in a simulated moving bed unit to recover para-xylene from a feed stream comprising a mixture of isomers of $C_8$ aromatics, with less need to perform major process piping and/or equipment construction and/or revamp work, thereby resulting in savings of time, manpower, material, and money.

These and other objectives are achieved by simultaneously supplying a second feed material stream into the adsorbent chamber of a countercurrent simulated moving bed process unit in accordance with the present invention. Further, these objectives and ideas can be utilized to improve recovery and purity in various systems. The various examples build on the general concept of the present invention, to provide a more efficient production system by providing a recycle stream into the system at a location having similar characteristics to the initial feed composition of the system.

Other advantages, benefits, and features of the invention will become apparent to those skilled in the art upon reading the detailed description of the invention.

DESCRIPTION OF THE PREFERRED EMBODIMENT

Although the disclosure hereof is sufficient to enable those skilled in the art to practice the invention, the physical embodiments herein disclosed merely exemplify the invention, which may be embodied in other specific structures. The scope of the invention is defined in the claims appended hereto.

In numerous processes described in the patent literature, zeolitic adsorbents are used to separate various hydrocarbons and other chemical compounds such as chlorinated or un-chlorinated aromatics. Another example of hydrocarbon separation by class is the recovery of either paraffins or aromatics from a feed mixture comprising both aromatics and paraffins. The subject invention can be employed in these separations or in the separation of other compounds including chiral compounds for use in pharmaceuticals and fine chemicals, oxygenates such as alcohols and ethers, carbohydrates such as sugars, and dimethyl naphthalenes. Efficiency is a more important factor in the commercial success of small units producing separated chiral compounds and other fine chemicals than for large scale units such as those producing para-xylene. The following description of the subject invention will, however, be presented basically in terms of the separation of various isomers of dialkyl substituted monocyclic aromatics, such as para-xylene isomer, from the other isomers of $C_8$ aromatics, which is normally performed in large scale units.

During the adsorption step of the process a feed mixture containing a mixture of isomers, such as xylene isomers, is contacted with the adsorbent at adsorption conditions and the desired isomer is selectively adsorbed and retained by the adsorbent while the other components of the feed mixture are relatively unabsorbed. The feed mixture may contain compounds other than isomers of the desired compound. For instance, a mixed xylene feed stream may contain ethylbenzene and/or $C_9$ aromatics. When the adsorbent contains a near equilibrium loading of the more selectively adsorbed isomer, it is referred to as a "rich" adsorbent. The unabsorbed raffinate components of the feed mixture are then removed from the interstitial void spaces between the particles of adsorbent and from the surface of the adsorbent. The adsorbed isomer is then recovered from the rich adsorbent by contacting the rich adsorbent with a stream comprising a desorbent material at desorption conditions. The desorbent displaces the desired isomer to form an extract stream, which is transferred to a fractionation zone for recovery of the desired isomer from the mixture containing the desired isomer and desorbent.

Processes for the adsorptive separation of para-xylene from other xylene isomers by simulated countercurrent adsorption are both widely described and widely practiced. These processes typically include at least three or four separate steps which are performed sequentially in separate zones within a mass of adsorbent retained in one or more vertical cylindrical adsorption chambers. The singular noun "chamber" is used herein to refer to one or more chambers. Each of these zones normally is formed from a plurality of beds of adsorbent, sometimes commonly referred to as either "beds" or "sub-bed", with the number of beds per zone ranging from 1 or 2 up to 8-10. The most widely practiced commercial process units typically contain about 24 beds. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams enter and leave the vertical adsorption chamber.

Briefly, in the first step, normally labeled as occurring in the adsorption zone or Zone I of the chamber, the feed stream is contacted with a selective adsorbent which adsorbs the desired isomer. This step removes the desired isomer from the flowing liquid. The depleted liquid and any desorbent which becomes admixed with it during passage through the adsorption zone are removed from the process as a process stream referred to as the raffinate stream.

The adsorbent in Zone I is surrounded by liquid which contains the undesired isomer(s), that is, with raffinate. This liquid is removed from the adsorbent in Zone II, referred to as a purification zone. In the purification zone the undesired raffinate components are flushed from the void volume and desorbed from the pore volume of the adsorbent bed by a material which is easily separated from the desired component by fractional distillation.

In Zone III of the adsorbent chamber the desired isomer is released from the adsorbent by exposing and flushing the adsorbent with a liquid called desorbent. The released desired isomer and accompanying desorbent are removed from the adsorbent in the form of a stream referred to herein as the extract stream.

Zone IV is a portion of the adsorbent located between Zones I and III which is used to segregate Zones I and III, and provide some of the desorbent flow for the desorption step. In Zone IV desorbent is partially removed from the adsorbent by a flowing mixture of desorbent and undesired components of the feed stream. The liquid flow through Zone IV prevents contamination of the liquid in Zone III by the liquid in Zone I by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563.

It is readily apparent that when a transfer line which is being used to transport a particular stream is left idle at the end of a "step" as the transfer lines are shifted, it will remain full of the compounds forming that stream until these compounds are removed from the line by a subsequent flowing stream. The residual compounds left in the volume of now unused transfer line will therefore be either withdrawn from the process as the initial part of a process stream flowing from the process, or introduced into the adsorbent chamber when the transfer line carries a stream into the adsorbent chamber as the transfer lines are shifted. As described above, those working in this art have recognized that the presence of these residual compounds in the transfer lines can have some detrimental effects on the performance of a simulated moving bed adsorptive separation process.

The precise amount of material which is used to flush a given transfer line beyond the amount required to flush the transfer line of its prior contents is not critically important, but measurement of this quantity is required. That is to say, it is believed there is only minimal back-mixing of liquids in the transfer lines, and that therefore the amount of flush liquid need not greatly exceed the total volume of the transfer line which is to be flushed. The transfer "line" may be in several parts linked together by valves or other connecting devices. A broad range of the required quantity of the flush liquid is from about 0.4 to about 2.5 times this total volume. A preferred quantity of the feed stream used to flush the raffinate line and any associated valving is from 0.5 to about 1.5 times this total volume.

In addition, as described above, since adsorption is an equilibrium mass-transfer process, the composition of the liquid in the selective pore volume of the adsorbent can be affected by changing the concentration of the liquid in the non-selective interstitial void volumes and pores of the adsorbent. Thus, most designers include a recycle stream to the upstream end of the purification zone to reflux para-xylene, which refluxing is expected to increase the concentration of para-xylene in the selective pore volume and to purge the transfer lines in question of components other than para-xylene.

Typical commercial practice involves the use of, in addition to the feed, raffinate, desorbent, and extract transfer lines, one or more additional transfer lines to accommodate the implementation of the above described para-xylene RECYCLE, LINE FLUSH and FLUSH OUT streams.

In accordance with the present invention, a stream of a second feed material is introduced into the chamber in either Zone II or Zone I as those zones are described above. The stream of the second feed material has a concentration of the desired compound that is different than the concentration of the desired compound in the first feed material stream. For maximum benefit, the second feed material is introduced at the location in the chamber at which the concentration of the desired compound in the second feed material most closely matches the concentration of the adsorbed component composition of material in the interstitial void inside the chamber, or the ratio of the desired to undesired isomers in the internal stream match the ratio of these components in the external stream. Accordingly, depending on the relative concentrations of the first and second feed materials, the second feed material stream may be introduced at a location either upstream or downstream of the location of the introduction of the first feed material stream. The present invention is thus designed to minimize changes to the concentration profiles in the adsorbent chamber at the transfer point on the adsorbent chamber where the second feed material stream is introduced, thus minimizing the quantity of the desired product that is contained in the raffinate stream.

It must be recognized that the subject invention is not directed to the technique of merely flushing a transfer line which carries liquid to and from the adsorbent chamber. It is therefore not limited to technology which merely involves flushing the beds of adsorbent material.

It must be further recognized that the subject invention is not directed to the technique of recycling either an extract product material stream or a raffinate product material stream back to the adsorbent chamber. It is therefore not limited to technology which merely involves recycling of such materials to the beds of adsorbent material.

It must be still further recognized that the subject invention is not directed to the technique of processing single feed material streams through the adsorbent chamber, but rather the processing of two or more feed material streams of differing compositions. It is therefore not limited to technology which involves the processing of single feed material streams to the beds of adsorbent material.

The terms "upstream" and "downstream" are used herein in their normal sense and are interpreted based upon the overall direction in which liquid is flowing in the adsorbent chamber. That is, if liquid is generally flowing downward through a vertical adsorbent chamber, the upstream is equivalent to an upward or higher location in the chamber. This is primarily important in describing the transfer line for the second feed stock that is used in the present invention. As will be described in detail below, in the present invention, with a second feed stream material having an adsorbed component concentration relatively greater than the adsorbed component concentration in the first feed stream material, it is most preferably the transfer line which was just used to inject the first feed material stream before the most recent incrementing (i.e., "step") of the transfer points during the simulation of countercurrent moving bed operation. Therefore, it is the transfer line just upstream of the transfer line presently used as the first feed material stream transfer line. This may in practice be one or more physical adsorbent chamber bed transfer lines away from the bed transfer line being used for feed, but is always downstream of (or below) the extract withdrawal point.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent, while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

In many cases, the concentration of the desired component in the second feed material stream is anticipated to be higher than the concentration in the first feed material stream. In those cases, the second feed material stream is introduced into the chamber upstream of the first feed material stream. Further, to optimize the overall performance of the chamber and its related equipment, it is highly desirable to utilize existing transfer lines to the extent possible.

Therefore, in the preferred embodiment, the second feed material stream is introduced into the chamber through the existing transfer line that was just flushed after carrying the first feed material stream to the chamber. That design minimizes the work and expense required to practice the invention without significant adverse effect on its benefits.

To be clear in the distinction between the present invention and the prior art, the use of an existing transfer line to carry either a pure or recycled desorbent material, extract material, single feed material, or raffinate material, as the case may be, in the practice of the present invention is merely a means to the end of the present invention. In fact, furthermore, the use of the single feed material or recycled extract material or raffinate material in the prior art is always present in the prior art only in conjunction with a single feed material, contrary to the practice of the present invention.

In further distinction of the present invention over the prior art, with respect to the introduction of the second feed material stream, larger amounts of material used as a flushing medium are generally beneficial as larger quantities of second feed material through the transfer line increase the feed processing capacity in the process unit, as it must be recognized that the flush material is passed into the adsorbent chamber at a transfer point on the adsorbent chamber where the adsorbed component composition of the interstitial void space liquid is determined by analysis or calculation to most closely match the adsorbed component composition of the second feed material stream.

Countercurrent simulated moving bed systems are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding system or by rotary disc valves as shown in U.S. Pat. Nos. 3,040,777 and 3,422,848. Equipment utilizing these principles can vary in size from the pilot plant scale shown in U.S. Pat. No. 3,706,812 to commercial petrochemical plant scale, with flow rates ranging from a few cc per hour to many thousands of gallons per hour. Large scale plants normally employ rotary valves having a port for each transfer line while small scale and high pressure units tend to use valves having only two or three ports. The present invention will normally be employed in an adsorptive separation process which simulates countercurrent movement of the adsorbent and surrounding liquid, but it may also be practiced in a cocurrent continuous process like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated by reference herein, for additional description of these adsorption fundamentals.

The practice of the subject invention requires no significant changes in adsorbent or desorbent composition. Further, in a preferred embodiment, no significant mechanical changes are required in the adsorbent chambers. For up to two distinct feeds, no new input streams are needed and the output streams are also essentially unchanged except for the added improvement of a reduction in the desorbent content of the output streams, thereby reducing the load on downstream product recovery units. The only significant required change to the process equipment is that needed to deliver a controlled quantity of the second feed material stream to the second feed material stream transfer line. These changes are preferably made in and near the equipment used to control the flow of the process streams to and from the adsorbent chamber in the case of the use of the flush transfer line essentially in the same manner as in the previously referred to Stine et al. patent, and in the case of the recycle transfer line, essentially in the same manner as in the previously referred to Broughton U.S. Pat. No. 3,732,325. That is, the subject process may be implemented on an existing process unit by a modification in the equipment which directs fluid flow. The amount of the respective material is preferably controlled by a single valve each on a single respective line through which the material in question flows before entering the line and valve system to be in question.

The practice of the subject invention is not believed related to or limited to the use of any particular adsorbent or adsorbent/desorbent combination. The only limitation is the effectiveness of the adsorbent/desorbent combination in the desired separation. Examples of adsorbents which may be used in the process of this invention include non-zeolitic molecular sieves including carbon-based molecular sieves, silicalite, and the crystalline aluminosilicates molecular sieves classified as X and Y zeolites. The adsorbent may or may not be a zeolite. The sorptive properties of one non-zeolitic molecular sieve, ALPO-5, are described in a paper printed in the Journal of Catalysis 111, 23-40 (1988). Details on the composition and synthesis of many of these microporous molecular sieves are provided in U.S. Pat. No. 4,793,984, which is incorporated by reference herein for this teaching. Information on adsorbents may also be obtained from U.S. Pat. Nos. 4,385,994; 4,605,492; 4,310,440; and, 4,440,871. Differing sieve/desorbent combinations are used for different separations. For instance, X zeolites, specifically X zeolites exchanged with barium or barium and potassium ions at their exchangeable sites, are the preferred adsorbents for p-xylene recovery from xylene mixtures.

The composition and structure of Zeolites is well know in the art and described in the references cited herein, hereby being incorporated herein by reference.

Those skilled in the art will appreciate that the performance of an adsorbent is greatly influenced by a number of factors not related to its composition such as operating conditions, feed stream composition, water content of the adsorbent, and the desorbent composition. The optimum adsorbent composition is therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500 degrees C. under an inert gas purge such as nitrogen for a period of time sufficient to achieve a constant weight. For p-xylene recovery it is often preferred that the water content of the adsorbent results in an LOI at 500 degrees C. of less than 7.0% and preferably within the range of from 0 to 6.5 wt %.

The zeolite will ordinarily be in the form of small crystals present in the particles in amounts ranging from about 75 to about 98 wt. % of the particle based on volatile-free composition. Volatile-free compositions are generally determined after the adsorbent has been calcined at 900 degrees C. in order to drive off all volatile matter. The remainder of the adsorbent will generally be the inorganic matrix present in intimate mixture with the small particles of the zeolite material. This matrix material may be an adjunct of the manufacturing process for the zeolite (for example, from the intentionally incomplete purification of the zeolite during its manufacture), or it may be added to relatively pure zeolite, but in either case its usual purpose is as a binder to aid in forming or agglomerating the zeolite into the hard particles.

Benzene, toluene, and p-diethylbenzene are normally described as suitable desorbents for para-xylene recovery in the references, with p-diethylbenzene (p-DEB) having become a commercial standard for the separation. P-DEB is a "heavy" desorbent (higher boiling than p-xylene) which allows for easier recovery of the desorbent from the extract and raffinate streams by fractional distillation.

At least portions of the extract stream and the raffinate stream are passed to separation means, typically fractional distillation columns, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream. The term "rich" is intended to indicate a concentration of the indicated compound or class of compounds greater than the concentration in the feed.

Feed mixtures which can be utilized in the process of this invention are typically prepared by fractional distillation. They may comprise para-xylene and at least one other $C_8$ aromatic isomer, and may also contain other hydrocarbons. Thus, the feed mixtures to the process of this invention can contain sizable quantities of $C_6$, $C_7$, and $C_9$ aromatics and may also contain quantities of straight or branched chain paraffins, cycloparaffins, or olefinic material having boiling points relatively close to the desired xylene isomer. The desired xylene may be the para, meta, or ortho isomer. The feed material streams can alternatively contain a mixture of isomers of other aromatic or paraffinic hydrocarbons. Some specific examples are cresol isomers, cymene isomers, and dimethyl naphthalene isomers. The subject process may also be employed to separate classes of compounds such as olefins from paraffins or straight chain paraffins from nonstraight chain; e.g., iso and cycloparaffins. The subject process may also be employed to separate classes of sugar compounds such as fructose from glucose.

Mixtures containing substantial quantities of para-xylene, other $C_8$ aromatic isomers, and other hydrocarbons and C9 aromatics generally are produced by catalytic naphtha reforming and/aromatic hydrocarbon isomerization processes. These processes are well known in the refining and petrochemical arts. In a catalytic naphtha reforming process, a naphtha boiling range feed is contacted with a platinum and halogen-containing catalyst at seventies selected to produce an effluent containing $C_8$ aromatic isomers. Generally, the reformate is then fractionated to concentrate the $C_8$ aromatic isomers into a $C_8$ fraction which will also contain co-boiling non-aromatics and some $C_7$ and $C_9$ aromatics. Feed mixtures for the process of this invention may also be obtained from isomerization and transalkylation processes. For instance, the transalkylation of mixtures of $C_7$ and/or $C_9$ aromatics produces xylene isomers. Xylene mixtures recovered from the adsorption zone which are deficient in one or more isomers can be isomerized, at isomerization conditions, to produce an effluent containing $C_8$ aromatic isomers, which can then be recycled to the adsorption zone for separation.

Adsorption conditions in general include a temperature range of from about 20 degrees to about 250 degrees C., with from about 60 degrees to about 200 degrees C. being more preferred for para-xylene separation. Adsorption conditions also include a pressure sufficient to maintain liquid phase, which may be from about atmospheric to 600 psig. Desorption conditions generally include the same range of temperatures and pressure as used for adsorption conditions. Different conditions may be preferred for other extract compounds.

Example

In order to verify the improvement expected from the present invention, a comparison was performed using a computerized model which has been shown to accurately predict and correlate with the actual operation of a given commercial scale simulated moving bed adsorptive separation unit used to recover para-xylene from a mixture of xylene isomers.

In this experiment, as is often the case commercially, it is assumed that the operator of the commercial process unit would have available to it two distinct sources of para-xylene containing feed stock. The simulated unit was assumed to have twenty-four beds of adsorbent which may commercially be divided between two columns and utilize a twenty-four port rotary valve to direct the flow of the process streams. For the purpose of explaining with further clarity the implementation and benefits of the present invention, but not meant to imply any limitation or requirement thereof, feed A is a first feed material stream originating from the isomerate xylene splitter column distillate product of a xylene isomerization process unit, and Feed B is a second feed material stream originating from the xylene column distillate product of a Toluene Disproportionation process unit. The two feed material streams contain the respective components as set out in Table 1.

Case I demonstrates the utility and benefits of the present invention by utilizing separate transfer points for the introduction of the two distinct feed material streams to the process unit of the present invention, while Case II shows the prior art method of mixing the two feed material streams into one combined feed material stream before the introduction thereof into the prior art process unit via a single transfer point feed material stream. In addition, the refiner would have as its objective to process in the process unit to recover 99.75 wt % purity para-xylene product at an acceptable recovery.

In addition, as shown in Case I, Table 1 shows the compositions of the first feed material stream and the second feed material stream of the present invention as well as the single combined feed material stream of the prior art. The model produced the different required adsorbent to feed ratios needed for the process unit to produce an extract having the required para-xylene recovery. These adsorbent to feed ratios were 0.95 using the combined feed material stream method of the prior art and were 0.75 using the first feed material stream and the second feed material stream of the present invention with the second feed material stream entering the adsorbent chamber through the line flush transfer line. These ratios translate into an approximately 27 volume percent increase in throughput capacity of the process unit.

TABLE 1

| | Feed Composition (wt. %) | | | | |
|---|---|---|---|---|---|
| | | I (Prior Art) Feed | | II (Present Invention) | |
| Case | I and II | | (Mixed) | Feed | Feed |
| Component | Extract | Raffinate | A + B | A | B |
| Non-aromatics | 0.00 | 0.4 | 0.2 | 0.3 | 0.0 |
| Ethylbenzene | 0.13 | 19.3 | 12.6 | 15.5 | 1.0 |
| Para-xylene | 99.75 | 1.2 | 35.8 | 22.5 | 89.0 |
| Meta-xylene | 0.08 | 54.5 | 35.4 | 42.2 | 8.0 |
| Ortho-xylene | 0.04 | 24.6 | 16.0 | 19.5 | 2.0 |

The following examples are included to further delineate the present invention. That is, the concept of injecting a second feed, or introducing any new input stream into a 'system', of different compositions, wherein the introduced or injected steam more closely matches the composition of the internal flowing liquid can be accomplished as described above in various situations. To make this idea more valuable, the invention can be used in the following systems to increase the capacity and/or decrease the consumption of energy within the system.

Example 2

Multiple Use Valves

Figure 1:
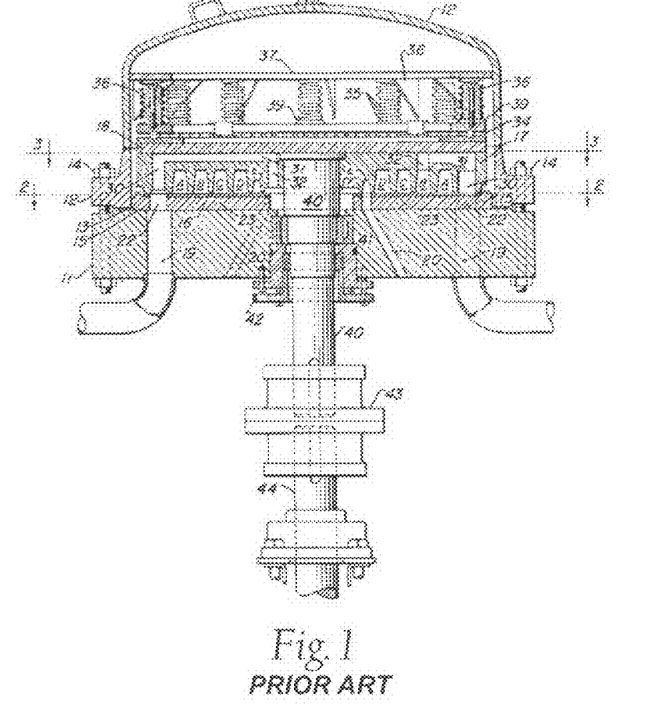
FIG. 1 is a prior art rotary valve that can be utilized by the present invention.
Figure 2:
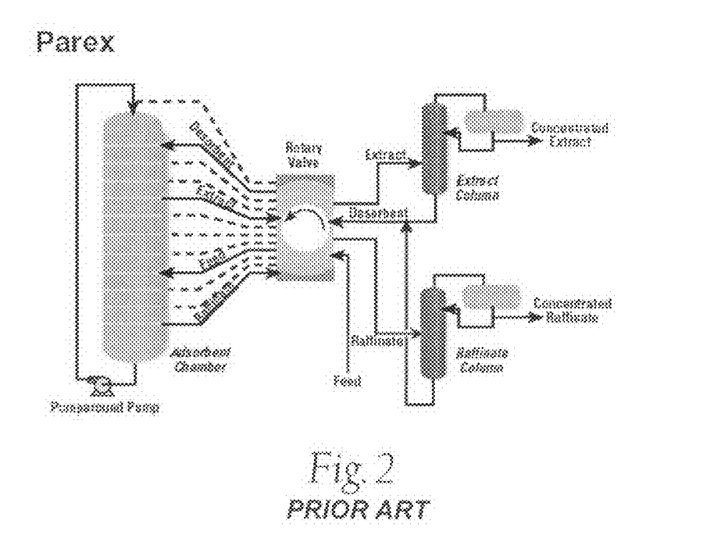
FIG. 2 is a flow chart of a prior art process.

As discussed above, systems referred to as simulated countercurrent moving bed units ("SMB") require a stream usually called line flush to purge the inventory of feed composition material in such piping before that same piping is used for the production/evolution of extract from the process unit. FIG. 1 shows a typical rotary valve (RV) and associated piping for use with the RV used in SMB processes. FIG. 2 shows a flow diagram of a typical SMB process. Since the volume of the liquid in such bed line and crossover pipe and RV track may be a large enough volume to contaminate the extract product, this line flushing is a critical step in making high purity product.

Figure 3:
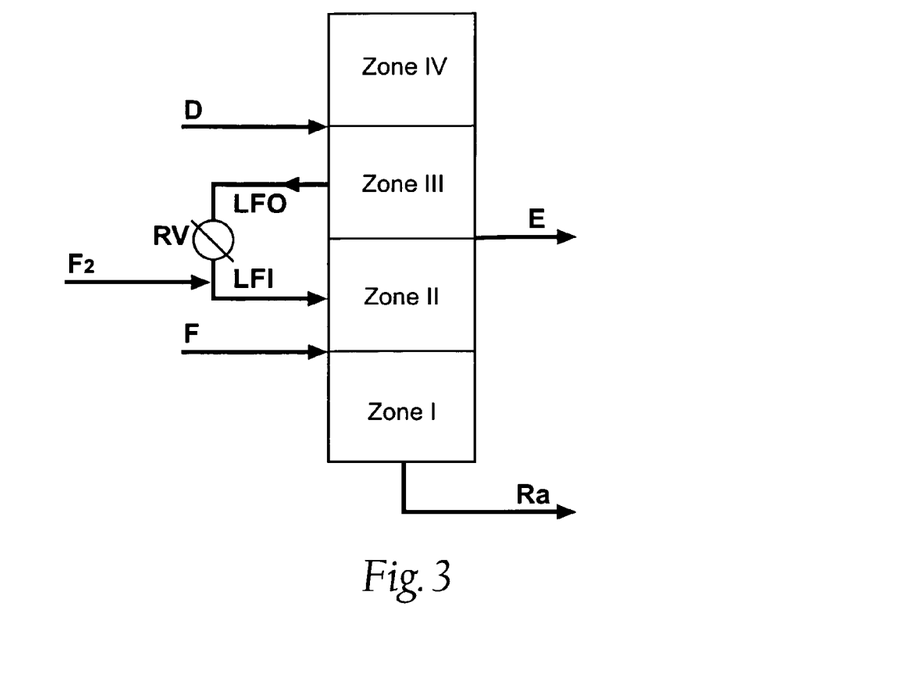
FIG. 3 is a flow chart of a process in accordance with the present invention.

FIG. 3 depicts a flow diagram according to the present invention. Because the line flush is between the feed point and the extract point, it is ideally suited to be also used for the injection of a second feed material ($F_2$) so long as that second feed material is of a paraxylene (px) concentration higher than the that contained in the original feed material (F). This can be done by adding a new line so that there are two feed points as disclosed above, or in a novel way described below by using some of the existing facilities for line flush by injecting the higher purity feed just prior to injecting the liquid for line flushing purposes.

In most cases, line flush is either a desorbent (D), or the return stream (i.e. a recycle stream) of another line flush OUT stream (LFO), or the line flush IN (LFI) stream. In the second case, the line flush OUT stream usually returns an inventory of extract in the piping, just after the lines have been used to evolve extract product liquid from the adsorbent chambers to the extract column. By properly re-sizing these flush lines, the facilities for line flush can also be used as aforesaid for the injection of the second feed. The idea is to first introduce into the flush IN piping, the second feed (higher px concentration) material and then introduce the line flush through such line flush IN (LFI) piping during each step of the SMB rotary valve. While this would involve an additional step in the control system logic used in the present scheme, it is easy to accomplish with the computational and logical power resident in modern control systems, resulting in a higher product purity of the eventual extract (E) and, as described above, higher capacity of the plant.

Example 3

Feeds with Low Concentrations of Ethylbenzene

The concepts discussed above can further exploit the low concentration of ethylbenzene (EB) in mixed xylene products obtained from toluene disproportionation process units (TDUs) by injecting this product stream higher in the purification zone, i.e., the section of the SMB that is between the feed point and the extract point. Licensors of this type of toluene disproportionation process include ToRay, UOP, ExxonMobil, and others. In these processes, the px concentration is typically 23% and ethylebenxene (EB) concentration is typically 2% on a volume basis. Most TDUs convert toluene into a mixture of benzene and mixed xylene isomers, or convert a mixture of toluene and $C_{9+}$ aromatics into benzene and mixed xylene isomers. The $C_8$ portion (i.e., the mixed xylene isomers) of the products is particularly valuable for processing in most SMB Units because of the low concentration of EB. For reference, the xylene stream from a Reforming Units contain 12 to 18% EB and 15 to 18% px. Thus, the ratio of px to EB is slightly greater than ~1. Xylenes from Disproportionation Units, in contrast, usually contain less than 3% EB and 22 to 24% px. Here, the ratio of px to EB is around 8. Since ethylbenzene is usually the most difficult component to remove from px in an SMB Unit, increasing the ratio of px to EB makes the SMB separation easier. For example, increasing the ratio to around 24 px to EB would make the separation easier.

Example 4

Feeds with High Concentrations of px

The present invention can also be used to exploit the high concentration of paraxylene in the highly selective disproportionation processes by injecting the second feed stream ($F_2$) stream between the feed point and the extract point in the SMB. Such processes that could be improved by incorporating the present invention are disproportionation processes used by UOP and ExxonMobil. ExxonMobil developed a catalyst for the disproportionation of toluene that produces a xylene stream that contains an unusually high concentration of paraxylene. In the products of these processes, the concentration px is typically 80% and the concentration of EB is typically 1% on a volume basis. At typical conditions in the reactor, the equilibrium concentration of para-xylene is about 23 to 24 mol percent. Based on public information, the $C_8$ portion of the product from the ExxonMobil catalyst contained anywhere from 70 to 95% px (molar basis).

There are two ways to exploit the unusually higher px composition of this material with the use of multiple feeds points as taught in the instant application. First, the liquid with the concentration of 70 to 95% px should be injected higher (closer to the extract point and further from the normal feed point) into the purification zone. In many SMB Units designed for the production of high purity px, there is a second line flush stream (secondary line flush) that uses desorbent to ensure that all of the feed material is purged from the piping and provide some extra "reflux" for the purification zone.

For the cases in which an SMB Unit is fed with xylenes from (a) Reforming Units, (b) Xylene Isomerization Units, (c) equilibrium-limited Disproportionation Units, and/or, finally, (d) a feed from a high px Disproportionation Unit, it would be advantageous to introduce these three feeds to three distinct corresponding feed points, the location of each point to be chosen closest to point in the SMB system such that the material being introduced into the SMB system at each such respective entry point is most similar to the corresponding composition of the px and/or EB concentration within the SMB system at such points with sometimes the more important criterion of the two being a match of the respective EB concentration. These could easily be the main feed point, the first flush point and the secondary flush point.

In an existing unit, it is not always possible to add another feed point or move the existing feed point or use the existing line flush line for a feed that, based on the teachings in this document, should be injected in a new position. In this case, it might be possible to reduce the concentration of ethylbenzene in the feed by using one of the feeds generated in a transalkylation unit or in an EB Cracking Unit, and then blending some or all of this material so the new composition more closely matches the composition of the liquid flowing in the adsorbent bed at the feed point.

Example 5

Feeds with Low Concentrations of Ethylbenzene

Just as it is possible to exploit high concentrations of paraxylene (px) (Example 4) according to the concepts and processes of the present invention, it is also possible to exploit the low concentrations of ethylbenzene in various processes. Processes that include feed streams from reforming units and pyrolysis naphtha hydrotreating units can utilize the current invention, especially when the feed streams first are sent to an EB Cracking Unit by injecting the feed stream into the purification zone, closer to the Extract point, above the location of the old feed. Examples of this type of process are used by Toray, ExxonMobil, and others.

Figure 4:
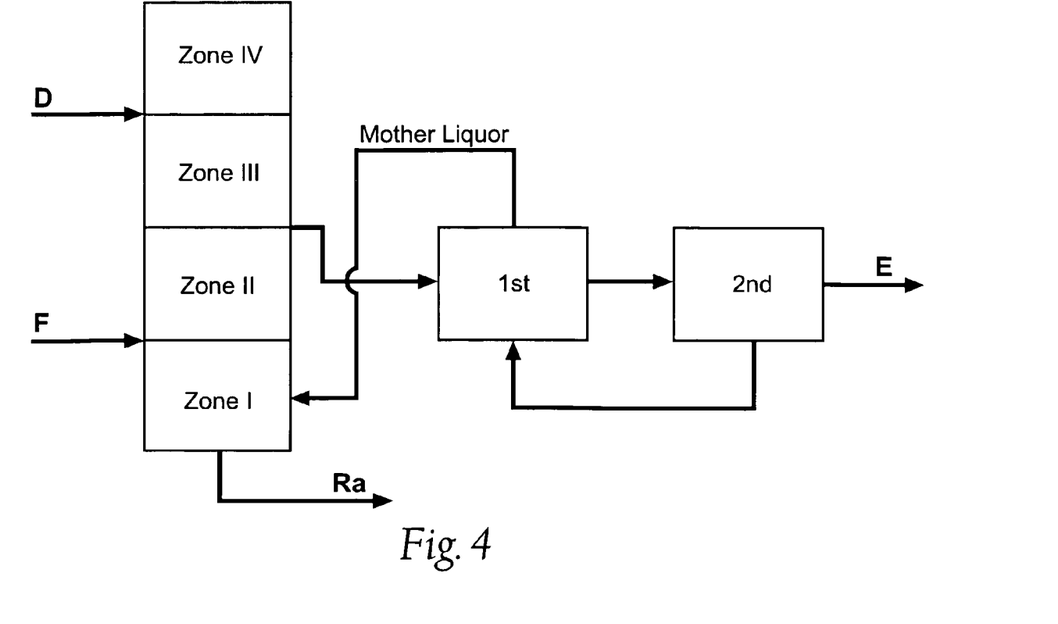
FIG. 4 is a flow chart of a hybrid process in accordance with the present invention.

A second method of providing streams with low concentrations of para-xylene and hence, high concentrations of ethylbenzene, which can incorporate the present invention, is to crack the ethylbenzene in the reformate before it enters the SMB portion of a para-xylene complex. When all of the reformate is treated in an EB Cracking Unit, the $C_8$ portion will have a high ratio of px to EB. To match this to the composition of the key compounds in the down flowing liquid, the feed point can be moved as taught in the present application, to a point having a relatively similar composition. Such a process is demonstrated in FIG. 4.

Example 6

SMB Units with Light Desorbent

Figure 5:
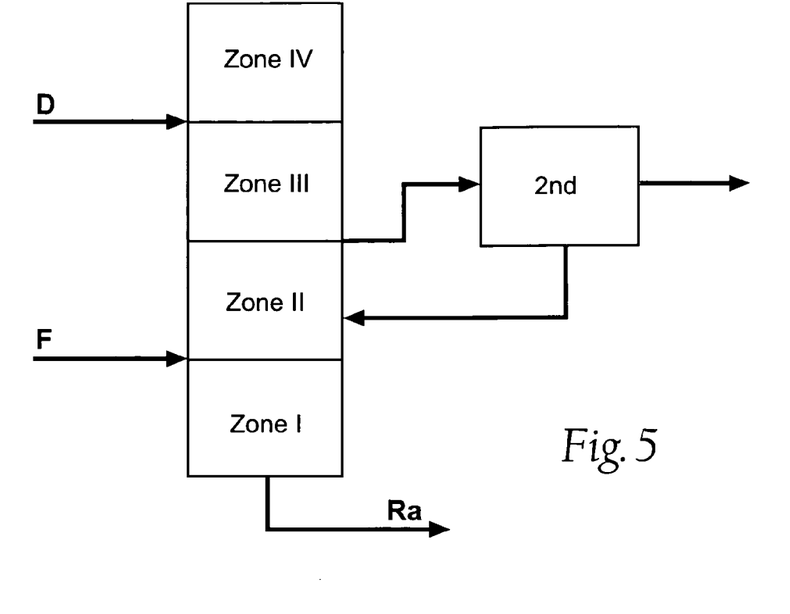
FIG. 5 is a further flow chart of a hybrid process in accordance with the present invention.

Certain processes, commonly referred to as Rejective Parex processes, are processes wherein the paraxylene in the system is not the most strongly adsorbed, and the px is generally passed to the raffinate (Ra) stream. Historically, SMB Units that produce high purity px using a light desorbent, such as toluene, have different B (selectivity) for ethylbenzene than for one or more of the other $C_8$ aromatics contained in the feed material. Since the EB selectivity is different in px SMB units that utilize a heavy desorbent, the positioning of the respective feed introduction points changes because the identity of the key components changes. The key components comprising the two components (often px and EB) in the feed mixture that have the most similar Ss are the most difficult to separate in the SMB unit. That is, because the location of the feed stream is determined by matching relative concentrations of the key components to their respective counterparts in the flowing liquid, the positioning of internal streams has to change because the identity of the key components themselves changes. However, the techniques described in the current application according to the present invention and described above still apply and bring with their application significant benefits in terms of increased capacity and reduced consumption of energy. FIG. 5 demonstrates the present invention being incorporated into such a process.

Example 7

Rejective Adsorption Units

Another example is units in which the primary product is the raffinate stream, often known as "rejective adsorption." One such process produces meta xylene. In this case, the para xylene and ethylbenzene are removed in the extract stream, and the ortho xylene is removed by fractionation. The resulting stream of raffinate is high purity meta xylene.

The benefits of matching the key components in the feed stream to the downflowing liquid at the feed point are virtually identical to the benefits in the units in which the primary product is the extract.

Example 8

Hybrid Solutions

Figure 6:
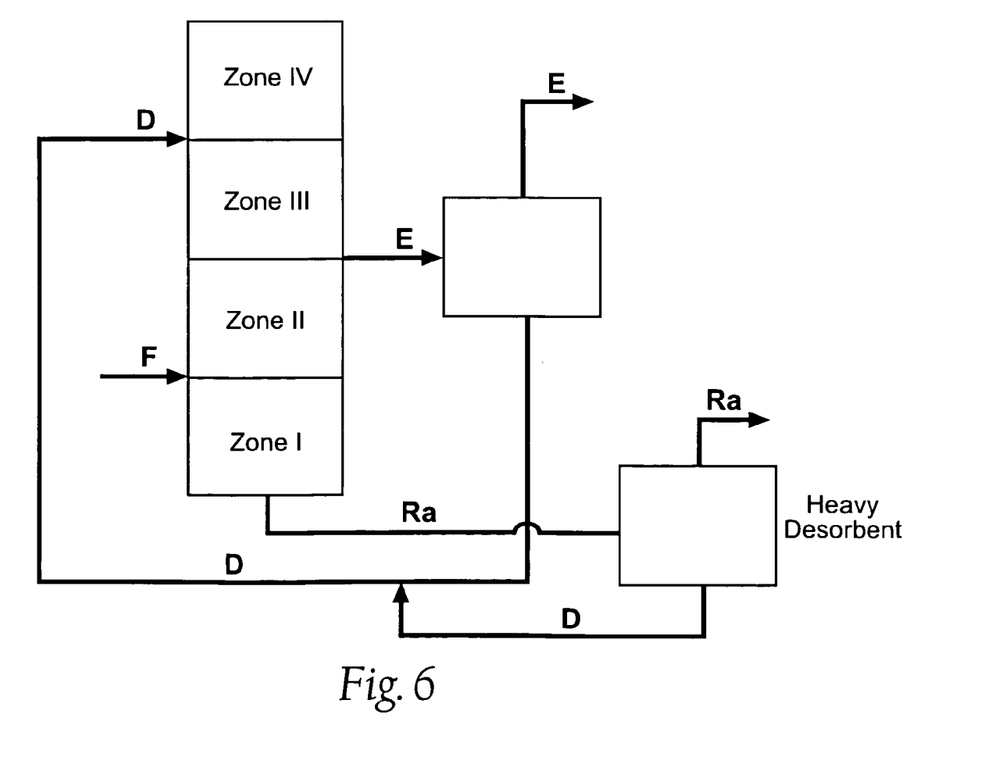
FIG. 6 is another flow chart of a hybrid process in accordance with the present invention demonstrating the removal of a heavy desorbent.
Figure 7:
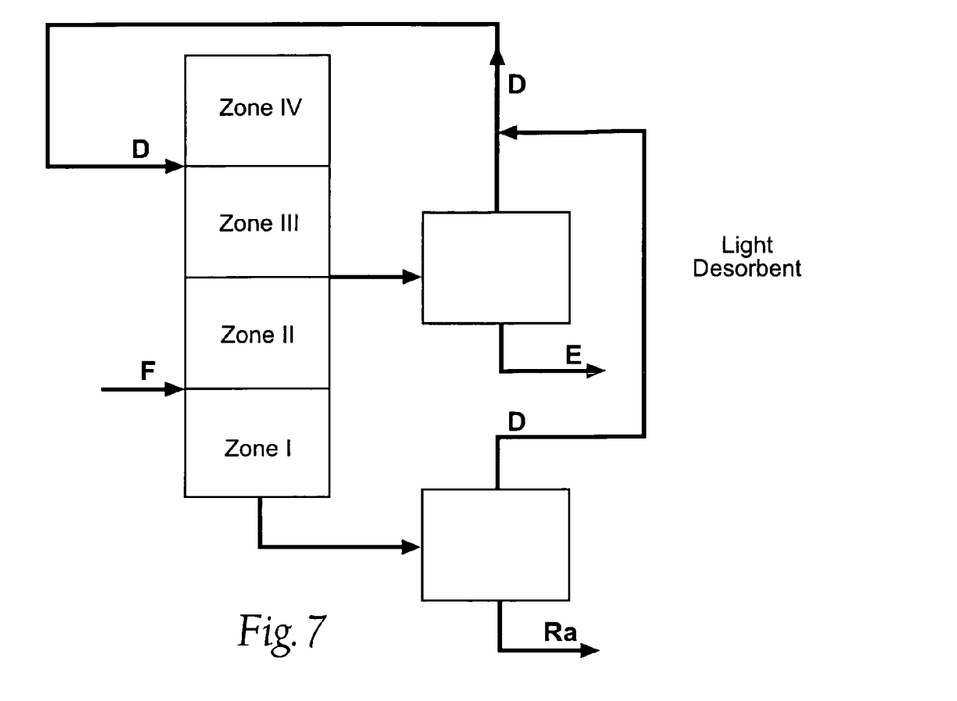
FIG. 7 is another flow chart of a hybrid process in accordance with the present invention demonstrating the removal of a heavy desorbent.

As previously discussed, there are two general processes used to separate para-xylene generally known and used in the art, The countercurrent simulated moving bed Parex® process technology and the older crystallizer process technology. While Parex processes provide great product recovery, they generally do not have the best purity. Conversely, crystallizer systems have good purity, with product recovery rates that are often less than desirable. Furthermore, the two processes are not necessarily compatible with one another, as they employ different technologies and different operating conditions. The present invention however further contemplates hybrid processes, incorporating both countercurrent simulated moving bed and crystallizer processes. The processes are based on the principle discussed above, wherein the second feed stream is fed into the respective system at a point where the concentration is similar to that of the first stream. Example of such hybrids are discussed below, and demonstrated in FIGS. 6 and 7.

1. Hybrid (I)—In the current state of the art of crystallizer technology, the "mother liquor", which is analogous to the raffinate stream in an SMB, typically contains 8-12% px, along with the remaining feed components to the crystallizer that were not present in Pp product (typically, 99.99% by weight), exits from the crystallizer. Typically the px in the crystallizer mother liquor is 'wasted' because it is merely recycled to the feed of an isomerization process unit, which thereupon upsets the isomerization process equilibrium dynamics. That is, the px in the feed to the isomerization unit: (a) detrimentally affects the catalytic equilibrium therein, and (b) could be viewed as 'taking up space' within the isomerization systems, which typically prefer the feed px to be minimized. In this case, such mother liquor would be fed into the SMB at a point in which, again, the px concentration of such material already most closely exists, e.g., Zone I, or the adsorption zone. The obvious benefits of such an arrangement are at least threefold, namely: (1) the px portion of the mother liquor no longer has to be reprocessed through the isomerization unit and does not 'take up space,' thereby increasing the capacity of the isomerization unit which will now be able to accommodate more of the fresh feed stream; (2) such px is more efficiently processed through the SMB at an appropriate point in its concentration profile to achieve separation of the px; and (3) by not overwhelming the isomerization catalyst with px, a more efficient reaction mixture from an equilibrium standpoint occurs in the ISOM reactor.

2. Hybrid (II)— A further novel configuration of px crystallization employs a combination of SMB and conventional crystallization technology, whereby, as separately disclosed in more detail in order to minimize the use of pure crystallization technology to purify px, a less rigorous crystallizer scheme is used. Such a system typically uses only one conversion stage instead of two, thereby once again recycling the mother liquor into the same SMB at a point in which the px concentration of such material already most closely exists, e.g., in this case Zone I, or the adsorption zone. That is, the recycled mother liquor would be expected to contain in this case typically more than 10% px and would be most efficiently fed (i.e. recycled) into Zone I, or the adsorption zone. Generally, this point reenters the SMB typically at a slightly different location than HYBRID (I), i.e., at a point closer to the feed point than what the feed point of HYBRID(I). The obvious benefits of such an arrangement are similar to the above Hybrid(I) case but amplified by the novel technological combination of SMB/Hybrid and Mother liquor recycle to SMB process.

3. Hybrid (Parex Processes)—In some cases, in order to improve the efficiency of the px separation unit, it is desirable to convert some percentage of EB in such material to substantially all mixed xylenes prior to the introduction of such material into the px separation unit. For the case where some of the feed which is to be separated in an SMB is first preprocessed through an EB Cracking process unit or sometimes with less conversion efficiency but eliminating the need to build an operate a separate EB Cracking process unit, such EB containing material is sent through a Xylene Isomerization Unit.

In the case of an SMB whether standalone or in an hybrid combination with a Crystallizer, the use of an appropriately selected adsorbent/desorbent system such that the system is more selective for EB (and/or other feed components) relative to the selectivity of such system for px, (i.e., a px rejective system) it is possible to operate the techniques specified in the parent invention in the same manner as in the paraxylene adsorptive system disclosed above. The advantage of a rejective system comprises the potential energy savings in the recovery of the rejected feed component (px product) from the rejective (raffinate) stream given the typical situation in which the concentration of the rejected component relative to the concentration of the desorbent in such raffinate stream is often higher thereby reducing the energy requirement to recover the rejected feed component from the raffinate stream mixture. In either case, the use of a second feed point is encompassed by the present invention, provided the placement of the stream is consistent with the positioning teachings, above.

4. Hybrid (Co-Current Process)

Figure 8:
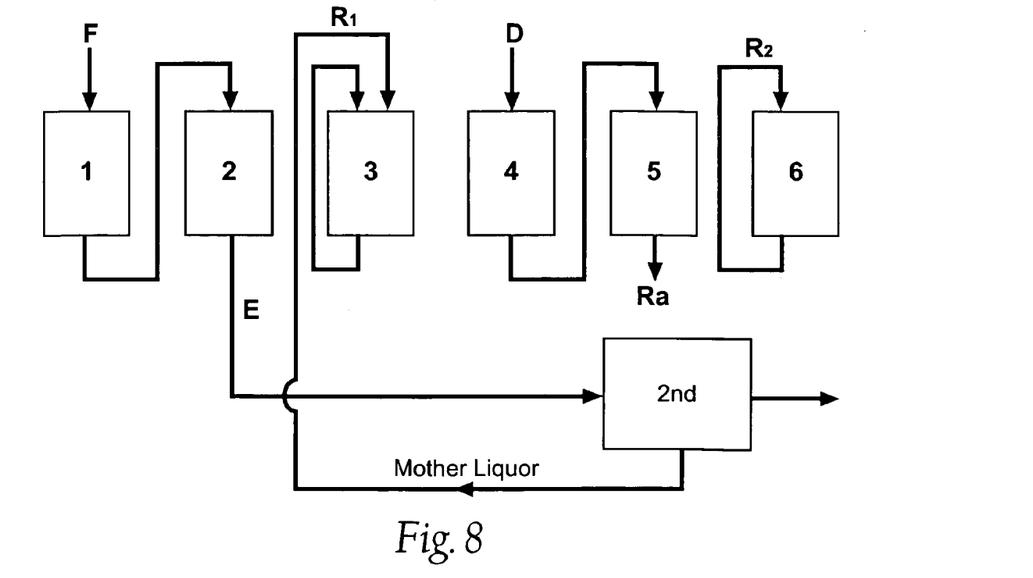
FIG. 8 is a flow process in accordance with the present invention, being utilized with an alternate separation process.

The present invention can also be employed in what are considered co-current (as opposed to countercurrent) SMB processes. That is, the present invention contemplates a hybrid process, comprising a co-current SMB feed pretreatment system in cooperation with a single stage crystallizer with a Mother Liquor Recycle stream. Such a process is depicted in FIG. 8. The flow scheme uses a co-current SMB to pre-treat the feed to the Crystallization Unit (to produce an extract stream of about 90% px and feed this to a small crystallization unit). The product from the crystallizer would have a concentration of 99.85% or higher px and the mother liquor concentration would be approximately 30 to 80% px. According to the present invention, the mother liquor stream would be sent to zone two, the purification section between the feed and the extract, in the SMB (see FIG. 8). Typically, the co-current SMB utilizes 2 to 6 beds in zone two instead of the 6 to 1-beds typically used in the counter-current SMB.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A simulated countercurrent adsorptive process for separating a desired chemical from a mixture of two or more chemical compounds within a multi-bed adsorbent chamber, the process comprising the steps of:
    introducing a stream of a first feed material having a first initial concentration of the desired compound;
    introducing a stream of a second feed material having a second initial concentration of the desired compound;
    flowing the stream of first feed material downstream through the adsorbent chamber;
    adsorbing the desired chemical from the first feed material to produce a first raffinate material;
    recycling a stream of material located downstream of said first feed material stream into said process at a location having a composition similar to said second initial concentration of said second feed material.

2. The process of claim 1 further comprising the steps of introducing a stream of flush material into the process, said recycle stream being fed into said stream of flush material.

3. The process of claim 1 wherein said steps of introducing first and second feed materials comprises the step of providing first and second materials each comprised of aromatic hydrocarbons.

4. The process of claim 1 wherein said steps of introducing first and second feed materials comprises the step of providing first and second materials each comprised of sugars.

5. The process of claim 1 wherein the second initial concentration is higher than the first initial concentration.

6. A simulated countercurrent adsorptive process for separating a desired chemical from a mixture of two or more chemical compounds within a multi-bed adsorbent chamber, the process comprising the steps of:
- introducing a stream of a first feed material having a first initial concentration of the desired compound;
- introducing a second feed material having a second initial concentration of the desired chemical compound into the adsorbent chamber upstream direction of the first stream of feed material;
- flowing the stream of first feed material downstream through the adsorbent chamber;
- flowing the stream of second feed material downstream through the adsorbent chamber;
- adsorbing the desired chemical from the first feed material to produce a first raffinate material;
- adsorbing the desired chemical compound from the second feed material by the selected adsorbent and thereby producing a second raffinate material;
- removing the second raffinate material from the adsorbent chamber at the second transfer point; and
- recycling a stream of material from said process into said process at a location having a composition similar to either of said first or said second initial concentration, said recycled stream being located downstream of said second feed stream or said first feed stream.

7. The process according to claim 6, wherein said recycled stream is reintroduced into the process at a location having a composition similar to said first initial concentration.

8. The process according to claim 6, wherein said recycled stream is reintroduced into the process at a location having a composition similar to said second initial concentration.

9. The process according to claim 6 further comprising the steps of:
- removing an extract stream from said adsorbent chamber; and
- passing said extract stream to a crystallizer system.

10. The process according to claim 9 wherein said recycle stream is removed from said crystallizer system.

11. The process according to claim 10, wherein said recycle stream comprises a light desorbent.

12. The process according to claim 10, wherein said recycle stream comprises a heavy desorbent.

13. The process according to claim 9 wherein said steps of introducing first and second feed materials comprises the step of providing first and second materials each comprised of aromatic hydrocarbons.

14. The process according to claim 13, wherein said recycle stream is reintroduced into said adsorbent stream downstream from said first and second streams of feed material.

15. A simulated adsorptive process for separating a desired chemical from a mixture of two or more chemical compounds, the process comprising the steps of:
- introducing a stream of a first feed material having a first initial concentration of the desired compound;
- introducing a second feed material having a second initial concentration of the desired chemical compound;
- flowing the stream of first feed material through the adsorbent process;
- flowing the stream of second feed material through the adsorbent process;
- adsorbing the desired chemical from the first feed material to produce a first raffinate material;
- adsorbing the desired chemical compound from the second feed material by the selected adsorbent and thereby producing a second raffinate material;
- removing the second raffinate material from the adsorbent chamber at a transfer point;
- recycling a stream of material located downstream of said first and/or said second feed material stream into said process.

16. The process according to claim 15, wherein said process is a countercurrent process.

17. The process according to claim 15, wherein said process is a co-current process.

18. The process according to claim 15, wherein said steps of introducing first and second feed materials comprises the step of providing first and second materials each comprised of aromatic hydrocarbons.

19. The process according to claim 15, wherein said steps of introducing first and second feed materials comprises the step of providing first and second materials each comprised of sugars.

20. The process according to claim 15, wherein said steps of introducing first and second feed materials comprises the step of providing first and second materials each comprised of xylenes.

* * * * *